US010149675B2

United States Patent
Orphanos et al.

(10) Patent No.: US 10,149,675 B2
(45) Date of Patent: *Dec. 11, 2018

(54) APPARATUS AND METHOD FOR REPAIRING TISSUE

(71) Applicant: DePuy Mitek, LLC, Raynham, MA (US)

(72) Inventors: Stephen J. Orphanos, Bridgewater, MA (US); William Arthur Roosa, Berkely, MA (US); Marc R. Helmick, Boston, MA (US); Stuart E. Fromm, Rapid City, SD (US)

(73) Assignee: DePuy Mitek, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,824

(22) Filed: Aug. 15, 2016

(65) Prior Publication Data

US 2016/0345957 A1    Dec. 1, 2016

Related U.S. Application Data

(60) Continuation of application No. 14/306,299, filed on Jun. 17, 2014, now Pat. No. 9,421,012, which is a
(Continued)

(51) Int. Cl.
*A61B 17/04* (2006.01)
*A61B 17/00* (2006.01)
*A61B 17/06* (2006.01)

(52) U.S. Cl.
CPC ...... *A61B 17/0401* (2013.01); *A61B 17/0469* (2013.01); *A61B 2017/00004* (2013.01);
(Continued)

(58) Field of Classification Search
CPC ............ A61B 17/0401; A61B 17/0469; A61B 2017/00004; A61B 2017/06052; A61B 2017/0464; A61B 2017/0417; A61B 2017/0409; A61B 2017/0459; A61B 2017/0475
See application file for complete search history.

(56) References Cited

U.S. PATENT DOCUMENTS

| 233,475 A | 10/1880 | Cook |
| 261,501 A | 7/1882 | Vandermark |

(Continued)

FOREIGN PATENT DOCUMENTS

| JP | 2007536007 A | 12/2007 |
| WO | WO 2005110244 A1 | 11/2005 |

OTHER PUBLICATIONS

DePuy Mitek, Inc. Orthocord Just Tie It, Knots, Arthroscopic Knot Tying Manual 2005.
(Continued)

*Primary Examiner* — Son Dang (57) ABSTRACT

Assemblies and methods suitable for knotless arthroscopic repair of tissue defects include two fixation members coupled by two limbs of suture comprising a continuous loop. A unidirectional restriction element that can be a preformed locking, sliding suture knot proximate to one of the fixation members, provides tensioning of the repair.

9 Claims, 8 Drawing Sheets

Related U.S. Application Data division of application No. 12/609,448, filed on Oct. 30, 2009, now Pat. No. 8,790,369.

(60) Provisional application No. 61/228,396, filed on Jul. 24, 2009.

(52) U.S. Cl.
CPC ............... *A61B 2017/0409* (2013.01); *A61B 2017/0417* (2013.01); *A61B 2017/0459* (2013.01); *A61B 2017/0464* (2013.01); *A61B 2017/0475* (2013.01); *A61B 2017/06052* (2013.01)

(56) References Cited

U.S. PATENT DOCUMENTS

| | | | |
|---|---|---|---|
| 4,235,238 A | 11/1980 | Ogiu | |
| 5,085,661 A | 2/1992 | Moss | |
| 5,320,633 A | 6/1994 | Allen | |
| 5,467,786 A | 11/1995 | Allen | |
| 5,470,337 A | 11/1995 | Moss | |
| 5,549,631 A | 8/1996 | Bonutti | |
| 5,601,571 A | 2/1997 | Moss | |
| 5,643,319 A | 7/1997 | Green | |
| 5,810,848 A | 9/1998 | Hayhurst | |
| 5,891,168 A | 4/1999 | Thal | |
| 6,056,320 A | 5/2000 | Khalifa | |
| 6,126,578 A | 10/2000 | Lapointe | |
| 6,143,006 A | 11/2000 | Chan | |
| 6,306,159 B1 | 10/2001 | Schwartz | |
| 6,500,184 B1 | 12/2002 | Chan | |
| 6,635,073 B2 | 10/2003 | Bonutti | |
| 6,767,037 B2 | 7/2004 | Wenstrom, Jr. | |
| 6,972,027 B2 | 12/2005 | Fallin | |
| 7,150,750 B2 | 12/2006 | Damarati | |
| 7,153,312 B1 | 12/2006 | Torrie | |
| 7,163,563 B2 | 1/2007 | Schwartz | |
| 7,235,091 B2 | 6/2007 | Thornes | |
| 7,357,810 B2 * | 4/2008 | Koyfman | A61B 17/0401 606/228 |
| 7,390,332 B2 * | 6/2008 | Selvitelli | A61B 17/0401 606/144 |
| 7,422,596 B2 | 9/2008 | Therin | |
| 7,572,275 B2 * | 8/2009 | Fallin | A61B 17/0401 606/232 |
| 7,601,165 B2 | 10/2009 | Stone | |
| 7,651,509 B2 | 1/2010 | Bojarski | |
| 7,887,551 B2 | 2/2011 | Bojarski | |
| 8,808,329 B2 * | 8/2014 | Bonutti | A61B 17/0401 606/232 |
| 9,833,231 B2 * | 12/2017 | Bojarski | A61B 17/0401 |
| 2002/0019649 A1 | 2/2002 | Sikora | |
| 2003/0130694 A1 * | 7/2003 | Bojarski | A61B 17/0401 606/228 |
| 2003/0236555 A1 * | 12/2003 | Thornes | A61B 17/0401 606/232 |
| 2004/0002734 A1 * | 1/2004 | Fallin | A61B 17/0401 606/232 |
| 2004/0210241 A1 | 10/2004 | James | |
| 2005/0033363 A1 | 2/2005 | Bojarski | |
| 2005/0251205 A1 | 11/2005 | Ewers | |
| 2005/0251208 A1 * | 11/2005 | Elmer | A61B 17/0401 606/232 |
| 2005/0251209 A1 * | 11/2005 | Saadat | A61B 17/0401 606/232 |
| 2005/0283192 A1 * | 12/2005 | Torrie | A61B 17/0401 606/228 |
| 2006/0064126 A1 | 3/2006 | Fallin | |
| 2006/0178680 A1 | 8/2006 | Nelson | |
| 2006/0190042 A1 | 8/2006 | Stone | |
| 2006/0217762 A1 | 9/2006 | Maahs | |
| 2006/0229623 A1 | 10/2006 | Bonutti | |
| 2006/0253132 A1 | 11/2006 | Evans | |
| 2006/0253152 A1 | 11/2006 | Evans | |
| 2006/0287676 A1 * | 12/2006 | Prajapati | A61L 17/145 606/228 |
| 2006/0293709 A1 * | 12/2006 | Bojarski | A61B 17/0401 606/232 |
| 2007/0027476 A1 | 2/2007 | Harris | |
| 2007/0083236 A1 * | 4/2007 | Sikora | A61B 17/0401 606/232 |
| 2007/0112383 A1 | 5/2007 | Conlon | |
| 2007/0112384 A1 | 5/2007 | Conlon | |
| 2007/0112425 A1 | 5/2007 | Schaller | |
| 2008/0065114 A1 | 3/2008 | Stone | |
| 2008/0077182 A1 | 3/2008 | Geissler | |
| 2008/0140092 A1 | 6/2008 | Stone | |
| 2008/0140093 A1 | 6/2008 | Stone | |
| 2008/0188893 A1 | 8/2008 | Selvitelli | |
| 2009/0228042 A1 | 9/2009 | Koogle, Jr. | |
| 2010/0114161 A1 | 5/2010 | Bojarski | |
| 2010/0114162 A1 | 5/2010 | Bojarski | |
| 2012/0016386 A1 | 1/2012 | Bojarski | |

OTHER PUBLICATIONS

F. Alan Barber, M.D. et al., Meniscal Repair Devices, Arthroscopy: The Journal of Arthroscopic and Related Surgery, Sep. 2000, pp. 613-618, vol. 16, No. 6.

F. Alan Barber, M.D. et al., Load to Failure Testing of New Meniscal Repair Devices, Arthroscopy: The Journal of Arthroscopic and Related Surgery, Jan. 2004, pp. 45-50, vol. 20, No. 1.

* cited by examiner

APPARATUS AND METHOD FOR REPAIRING TISSUE

FIELD OF THE INVENTION

The invention relates generally to devices and methods for repairing tissue. More specifically, the invention relates to suture anchoring devices and methods for arthroscopic repair of tissue defects.

BACKGROUND OF THE INVENTION

A variety of injuries and conditions require repair of soft tissue damage, or reattachment of soft tissue to bone and/or surrounding tissue. For example, when otherwise healthy tissue has been torn away from a bone, such as a shoulder rotator cuff tendon being partially or completely torn from a humerus (a rotator cuff tear), surgery is often required to reattach the tissue to the bone, to allow healing and a natural reattachment to occur. A number of devices and methods have been developed for performing these surgical repairs, some of the more successful methods including the use of suture anchors or, generically, "suture fixation members," which typically include an anchor body having one or more suture attachment feature, and a tissue or bone engaging feature for retaining the suture anchor within or adjacent to the tissue or bone. Depending on the specific injury, one or more suture anchor connected to, or interconnected by, one or more segment of suture, may used to perform the repair.

Surgery can also be required when a tear occurs in the substance of a single type of tissue, for example in the meniscus of the knee (a meniscal tear). One method of repairing such a tear is to stitch it closed by passing a length of suture through the tissue and tying the suture. Suture can also be used in conjunction with one or more suture anchor to repair such tissue tears. Sutures can be fastened to suture anchors and to tissue using knots tied by the surgeon during a repair procedure, or using "knotless" devices and methods, where one or more anchor and one or more suture can be connected and tensioned without the surgeon needing to tie knots during the surgery. Knotless anchoring is of particular utility for minimally invasive surgeries such as endoscopic or arthroscopic repairs, where the surgeon must remotely manipulate the suture at the surgical site using tools inserted through a small diameter cannula or endoscopic tube, which can make the knotting process difficult and tedious.

Various methods are used to provide knotless anchoring, including anchors that automatically lock a suture in position as the anchor is deployed in tissue, anchor components that can controllably lock a suture to the anchor after the anchor is deployed, devices that enable a suture to slide through them in one direction only, and preformed knots that can be tightened by the surgeon using a simple tool, or by tensioning one or more suture strand extending from the knot.

While many suture anchoring systems have been developed for repairing torn tissue, current devices are not without their drawbacks. Some knots or other anchor components may "stand proud" above the repaired tissue's surface especially that surface facing weight bearing contact with bone such as the interface between the femur and the meniscus and interfere with movement and healing of, for example, articulating joint tissue, or the knot's position relative to the anchor or nearby tissue may not be fully under the surgeon's control, in some situations providing a less than optimal repair. In surgeries where two or more suture anchors are joined by suture to repair an injury, any knots or joined suture segments positioned along the suture connecting the anchors to one another can become stress points that limit the ultimate strength of the surgical repair or contribute to surgical trauma.

Accordingly, there remains a need for improved methods and devices for repairing torn or damaged tissue, and in particular for methods and devices suitable for arthroscopic repair of torn or otherwise damaged tissue using suture anchors. There also remains a need for methods and devices that reduce the risk of damage to the tissue being repaired, and that provide a low profile to eliminate interference with movement and healing in articulating joints.

SUMMARY OF THE INVENTION

Accordingly, the present invention provides embodiments of suture anchoring devices and methods for repairing damaged tissue. An apparatus according to the present invention comprises first and second fixation members, with each of the first and the second fixation members having a first surface, an opposing second surface, first and second through openings defined between the first surface and the second surface. A flexible element couples the first and the second fixation members, the flexible element having a first end, a second end and a length therebetween which extends from the first end, in order, along a first end section of suture, through the first opening in the first fixation member from the respective first surface to the respective second surface, through the first opening in the second fixation member from the respective second surface to the respective first surface, through the second opening in the second fixation member from the respective first surface to the respective second surface, through the second opening in the first fixation member from the respective second surface to the respective first surface, and along a second end section of suture. The first fixation member has a third through opening defined between the respective first and second surface. A sliding, locking knot is formed between the first end section and the second end section, with the first end section positioned slidably through the knot and extending from the knot and through the third opening from the first surface to the second surface.

In one aspect of the invention, the first, second and third openings through the first fixation member are arranged in substantially a straight line along the respective first and second surface. Preferably, the first and the second fixation members comprise rounded surfaces between adjacent openings on each respective surface, for sliding the flexible element therealong. In one aspect of the invention each of the openings has a substantially circular cross section. Alternatively, one or more of the openings has an elongated cross section. Preferably, tension applied to the second end section with respect to the first fixation member is effective to decrease a distance between the first and the second fixation member along the flexible member coupling the first and the second fixation member.

In one aspect of the invention, the first and the second fixation members further comprises a substantially linear groove in each of the respective first and second surfaces, the groove extending from a first end of the respective surface to an opposite end of the respective surface, the groove in the second surface being substantially parallel to the groove in the first surface. A delivery device has an elongated delivery member within which at least a portion of each of the first and the second fixation members, coupled by the flexible element, is longitudinally and slidably received, preferably with their grooves slidably engaged with a slot in the delivery member.

Preferably, the flexible element comprises a suture. In one aspect of the invention the flexible element comprises polyethylene. In another aspect of the invention the flexible element comprises polyethylene and a bioabsorbable polymer, preferably the bioabsorbable polymer comprises polydioxanone.

Preferably, the sliding, locking knot is a bunt line knot.

Preferably, a delivery device is provided which comprises a cannula having a proximal end and a distal end, and a longitudinal slot in a wall of the cannula which extends from the distal end toward the proximal end, the cannula is defined by opposing longitudinal edges along the slot. The first and the second fixation device are received in the cannula along the slot, with the slot edges slidingly engaged in respective grooves in each of the first and the second fixation device. Preferably, a deployment rod is positioned in the cannula, a handle mechanically couples to the proximal end of the cannula, and a manually actuable member is associated with the handle to translate the deployment rod distally in the cannula for expelling one of the first and the second fixation device slidingly from the distal end of the cannula.

An apparatus according to the present invention comprises first and second fixation members. Each of the first and the second fixation members having a first surface and an opposing second surface, first, second and third through openings defined between the first surface and the second surface of the first fixation device, and one or more through openings defined between the first surface and the second surface of the second fixation device. A flexible element couples the first and the second fixation members. It has a first end, a second end and a length therebetween, the length extending from the first end, in order, along a first end section of suture, through the first opening in the first fixation member from the respective first surface to the respective second surface, through at least one of the one or more opening in the second fixation member from the respective second surface to the respective first surface, through the second opening in the first fixation member from the respective second surface to the respective first surface, and along a second end section of suture. A sliding, locking knot is formed between the first end section and the second end section, the second end section extending from the knot and through the third opening from the first surface to the second surface.

An apparatus according to the present invention comprises first and second fixation members coupled by two continuous sections of suture extending therebetween. The first fixation member has a first surface and an opposing second surface. The two suture sections are continuous with one another and slidable through an opening through the second fixation member. Each of the two sections of suture extend through respective first and second through openings in the first fixation member from the second surface to the first surface. A sliding, locking knot joins the two continuous sections of suture adjacent to the first surface. A third through opening extends between the first surface and the second surface and one of the two continuous sections of suture extends from the knot and through the third opening from the first surface to the second surface.

An apparatus according to the present invention provides for repairing a defect in a body tissue. It comprises a first fixation member having a first surface and an opposing second surface, and first, second and third through openings between the first and the second surface. A second fixation member has one or more through openings. The first and the second fixation members are coupled by a continuous length of suture defining a loop joined by a sliding, locking knot positioned substantially adjacent to the first side of the first fixation member. The loop extends from the knot slidably through, in order, the first opening in the first fixation member, at least one of the one or more openings in the second fixation member, the second opening of the first fixation member, and returns to the knot. An end section of the continuous length of suture extends from the knot and through the third opening of the first fixation member from the first side to the second side. Tensioning the end section with respect to the first fixation member is effective to shorten the loop.

Preferably, the knot is a bunt line knot, and also preferably the second surface is adapted to contact the tissue being repaired, and the knot is maintained adjacent to the first surface.

A method according to the present invention provides for repairing a defect in a body tissue. The method comprises the steps of: passing a first fixation member along a first delivery path through the tissue to a first location on a first surface area of the tissue, the first fixation member having opposing first and second surfaces, a sliding and locking suture knot adjacent to the first surface, the suture knot comprising suture, three limbs of suture extending from the second surface along the delivery path, the three limbs of suture each continuous with the suture comprising the knot, a first two of the three limbs together comprising a continuous loop of suture slidingly connected to a second fixation member, the loop having a loop length; tensioning at least one of the three sections of suture to deploy the second surface against the tissue at the first location; passing the second fixation member along a second delivery path through the tissue to a second location on a second surface area of the tissue; and tensioning the third limb of suture to reduce the loop length between the first fixation member and the second fixation member.

Preferably, tensioning the third limb of suture deploys the second fixation member against the tissue at the second location and also applies a compressive force to reduce the tissue defect.

Preferably, the first fixation member comprises a first, a second, and a third through opening between the first side and the second side, each of the first, second and third limb positioned through the respective opening and the second fixation member comprises two through openings, and the loop passes slidingly through both openings.

In one aspect of the invention, the first location and the second location are on a single surface of the tissue. In another aspect of the invention the first location and the second location are on opposing surfaces of the tissue.

An apparatus according to the claimed invention comprises a first fixation member having opposing first and second surfaces. A sliding and locking suture knot sits adjacent to the first surface. It comprises suture, three limbs of which extend from the second surface, are continuous with the suture comprising the knot, each of which are positioned through a respective through opening between the first surface and the second surface. A first two of the three limbs together comprise a continuous loop of suture slidingly connected to a second fixation member. The loop has a loop length. The knot is configured so that tension applied to the third limb with respect to the first fixation member is effective to reduce the loop length An apparatus according to the present invention comprises a first fixation member having opposing first and second surfaces, with first, second and third through openings extending between the first and the second surfaces, and respective first, second and third limbs of suture positioned through the respective first, second and third openings. The first and the third limbs are positioned slidably through the respective first and third opening and the first and the second limbs are continuous with one another to form a suture loop extending from the second surface. A second fixation member has one or more opening therethrough with the loop positioned slidably through at least one of the one or more openings through the second fixation member. A restriction element is associated with the first fixation member and is adapted to slidably pass suture therethrough in a first direction, but not in a second, opposite direction. The first and the third limbs are continuous with one passing through the restriction member adjacent the first surface. Tension applied to the third limb with respect to the first fixation member is effective to reduce the loop length by sliding the third and the first limb through the respective third and first opening.

An apparatus according to the claimed invention comprises a first fixation member and a second fixation member, with at least one opening through the second fixation member. Two limbs of suture form a continuous loop of suture extending from the first fixation member with a portion of the loop positioned slidably through the at least one opening through the second fixation member. The first fixation member comprises a restriction element through which an extension of one of the two limbs is positioned to pass slidingly in a first longitudinal direction, but is restricted from sliding in a second, opposite longitudinal direction. The two limbs and the extension extending from a common surface of the first fixation member.

An apparatus according to the present invention provides for repairing a body tissue having a surface. The apparatus comprises first and second fixation members, each of the first and the second fixation members having a respective contact surface adapted to be positioned in contact with the tissue surface. A continuous loop of suture extends between respective contact surfaces of the first and the second fixation member, the loop having a length, and being slidably positioned through one or more opening through the second fixation member. A tensioning limb of suture extends from the contact surface of the first fixation member so that tension applied to the tensioning limb with respect to the first fixation member is effective to reduce the length of the loop.

Preferably, the tensioning limb is continuous with the suture comprising the loop. In one aspect of the invention the first fixation member comprises a locking, sliding knot through which the tensioning limb is positioned. Preferably, the sliding knot is position adjacent a non-contact surface on the first fixation member, the non-contact surface being opposed and opposite to the contact surface. Preferably, the tensioning limb can pass slidingly through the knot in a first longitudinal direction along the suture, and is restricted from sliding through the knot in an opposite longitudinal direction.

A method according to the present invention provides for repairing a defect in meniscus. The meniscus has a first surface facing an associated femur and a second, opposing surface away from the femur and away from a tibia. The method comprises the steps of: placing a first fixation member against the second surface at a first location adjacent the defect; placing a second fixation member against the second surface at a second location adjacent the defect; arranging a flexible member between the first fixation member and the second fixation member across the defect, the flexible member passing through the meniscus and comprising a loop upon which the second fixation member is slidably affixed and which comprises a slip knot affixed to the flexible member adjacent the first fixation member beyond the second surface; and tensioning a portion of the flexible member through the slip knot to shorten the loop and close the defect.

Preferably, the first fixation member has a first side and a second side with the slip knot abutting the first side and wherein the method comprises the step of placing the second side against the second surface on the meniscus.

DESCRIPTION OF THE DRAWINGS

This invention is described with particularity in the appended claims. The above and further aspects of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Devices and methods of the present invention enable a surgeon to consistently and reliably repair tissue tears and separations using two fixation members interconnected by continuous segments of suture. Surgeries using the devices of the present invention are performed without the surgeon having to tie any suture knots, and are particularly suitable for performing arthroscopic or endoscopic repairs. Repairs performed using the present invention leave no knots, suture joints or other potential stress points along the suture interconnecting the fixation devices, reproducibly position any knots away from tissue areas that are particularly susceptible to post-surgical damage, for example, articulating tissue surfaces. It is to be understood that particular devices and methods disclosed herein are exemplary and not limiting of the present invention, for example, embodiments illustrated herein for repairing in-substance injuries to soft tissue, such as the meniscus of the knee, can be equally applied for repairing partial or complete tears in another type of soft tissue, or for repairing partial or complete separations of one type of tissue from another, for example, separation of a tendon or ligament from a bone.

Figure 1:
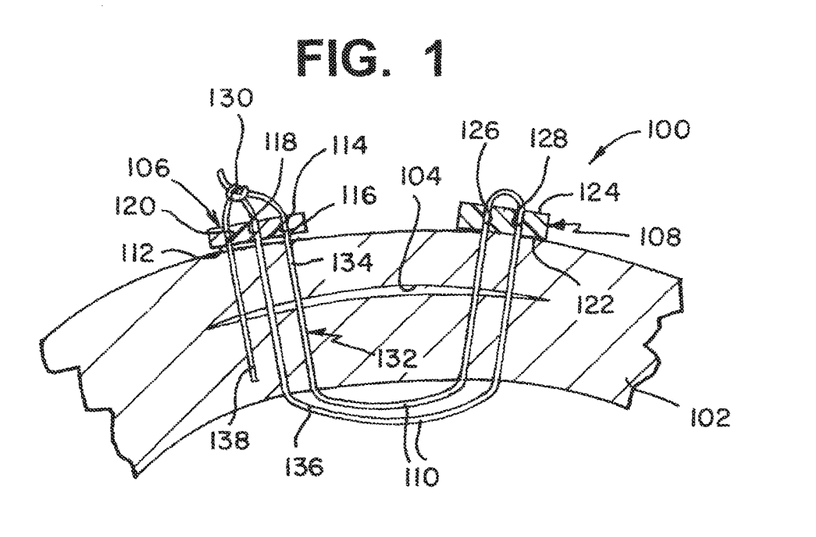
FIG. 1 is a cross sectional view of an exemplary embodiment of a tissue repair assembly of the present invention, implanted in a body tissue.

Referring more particularly to the figures, FIG. 1 schematically illustrates a cross sectional view of an exemplary embodiment of a tissue repair assembly 100 of the present invention implanted in a body tissue 102, for repairing a defect 104 in the tissue 102. In an exemplary embodiment, the tissue 102 is a meniscus in a knee and the defect 104 is a meniscal tear. In another embodiment, the tissue 102 is another type of body tissue. In yet another embodiment, the defect 104 is a separation between two different types of body tissue.

The repair assembly 100 is seen to comprise a first fixation member 106, a second fixation member 108 and a continuous flexible element 110 interconnecting and extending through the first 106 and the second fixation member 108. The flexible element 110 can comprise any type of flexible element suitable for implantation and use in making surgical repairs, and is hereinafter referred to as "suture." The suture 110 can be any type of suture including suture fabricated using natural materials such as silk, and synthetic materials such as polyethylene terephthalate (PET) or other polyester materials. The suture 110 can be bioabsorbable, partially bioabsorbable, or nonabsorbable, and can have a circular cross section or another cross section. In one embodiment, the suture 110 is partially bioabsorbable, comprising polyethylene as a nonabsorbable component, and polydioxanone as a bioabsorbable component.

The first fixation member 106 is seen to comprise a first tissue-contact surface 112, a first back surface 114 and a first 116, a second 118 and a third through opening 120 between the first tissue-contact surface 112 and the first back surface 114. The second fixation member 108 is seen to comprise a second tissue contact surface 122, a second back surface 124 and a respective first 126 and second through opening 128 between the respective tissue contact 122 and back surface 124. In an embodiment, one or more of the respective through openings is adapted for slidably passing the suture 110 therethrough. In a further embodiment, the respective tissue contact and back surfaces between adjacent openings through each the first 106 and the second anchor 108 are rounded to optimize the slidability of the suture 110 through and among the respective openings. In one embodiment, the cross section of each of the openings is round. In another embodiment, one or more of the openings is elongated in a direction transverse to a line connecting the one or more opening with an adjacent opening through the respective fixation member.

The suture 110 is seen to comprise a locking, sliding knot 120 adjacent to the back surface 114 of the first fixation member 106. The suture is seen to comprise a continuous loop section 132 extending from the locking, sliding knot 130, the loop section 132 comprising a first limb 134 and a second limb 136. The first limb 134 is seen to extend from the locking, sliding knot 130 toward and through the respective first opening 116 in the first fixation member 106 from the respective back surface 114 to the respective tissue-contact surface 112, toward and through the respective first opening 126 in the second fixation member 108, from the respective tissue-contact surface 122 to the respective back surface 124. Continuing from the back surface 124 of the second fixation member 108, the first limb 134 is seen to be continuous with the second limb 136 in the loop 132, returning through the respective second opening 128 from the back surface 124 to the tissue-contact surface 122 of the second fixation member 108, toward and through the respective second opening 118 in the first fixation member 106, to the locking, sliding knot 130, completing the loop 132. In an embodiment, the loop 132 is positioned slidably through each of the respective first and second opening through each of the first 106 and the second fixation member 108.

In an embodiment, the second limb 136 is connected fixedly to the locking, sliding knot 130 and the first limb 134 extends slidably through the locking, sliding knot 130, to and continuous with a tensioning limb 138 that extends from the locking, sliding knot 130 toward and through the third opening 140 from the respective back side 114 to the tissue contact side 112 of the first anchor 106. An application of tension to the tensioning limb 138 with respect to the first anchor 106 is effective to slidingly draw suture from the loop 132 through the respective first opening in the first fixation member, the locking, sliding knot 130 and the third opening 120, shortening the loop 132 as the transmitted tension further draws a portion of the second limb 136 slidingly through the respective second 128 and first opening 126 in the second fixation member 108. In an embodiment, shortening the loop 132 applies a compressive force for closing the defect 104 in the tissue 102. It is to be noted that for illustrative purposes in FIG. 1, the various suture limbs 134, 136 and 138 are shown laterally separated from one another through the tissue 102, but that in an actual tissue repair using the tissue repair assembly 100, the various suture limbs 134, 136, 138 follow a substantially common path adjacent to one another through the tissue 102.

Figure 2A:
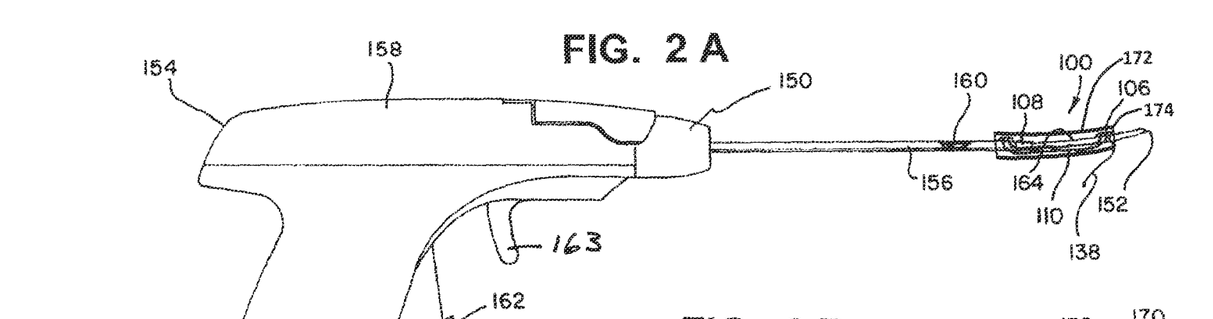
FIG. 2A is a side elevation view of an exemplary embodiment of a tissue repair assembly of the present invention, disposed on a delivery device of the present invention.
Figures 2B, 2C:
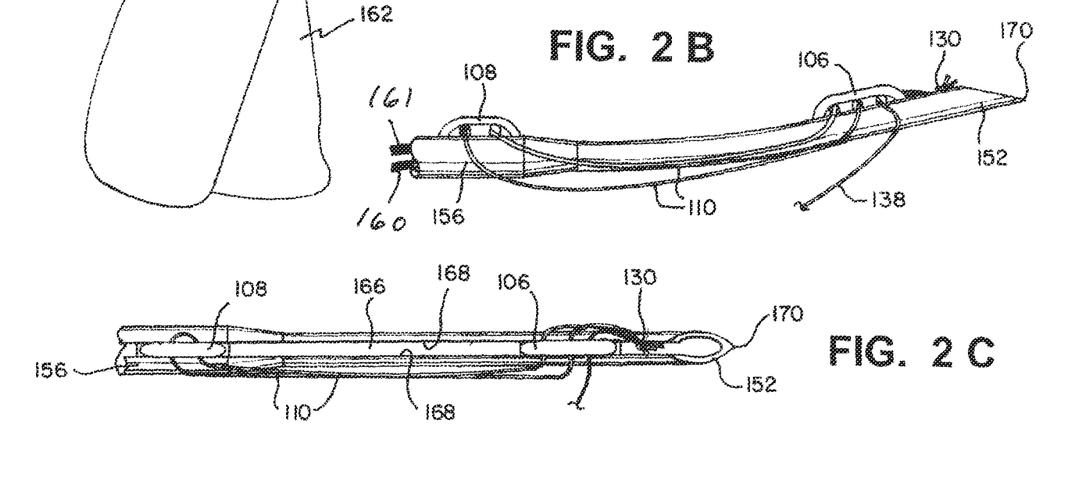
FIGS. 2B and 2C are side elevation and top views, respectively, of a distal portion of the delivery tool illustrated in FIG. 2A.

FIG. 2A schematically illustrates a side view of an exemplary embodiment of the tissue repair assembly 100, disposed on a delivery device 150 of the present invention, the delivery device 150 having a distal end 152 and a proximal end 154. The delivery device 150 is seen to comprise a substantially tubular distal delivery member 156 extending distally from a proximal handle 158. FIGS. 2B and 2C illustrate more detailed views of a distal portion of the delivery member 156 with the tissue repair assembly 100 disposed thereon, in respective side and top views.

The first 106 and the second fixation member 108, with at least a portion of the suture 110 extending therebetween, are seen to be slidably retained along and at least partially within the delivery member 156. The delivery device 150 is also seen to comprise at least one deployment rod 160 distally slidable in the delivery member 156 for sequentially expelling the first 106 and the second fixation member 108 distally from the delivery member 156. The handle 158 is seen to comprise at least one manually actuable trigger 162, actuable for distally sliding one of the at least one deployment rod 160. In one embodiment, as illustrated in FIG. 2A, the delivery member 156 comprises a curve 164 along its length. In another embodiment (not shown), the delivery member 156 is substantially straight between the handle 158 and the distal end 152.

In an embodiment, each of the first 106 and the second fixation members 108 is slidably retained in a longitudinal slot 166 in the delivery member 156, the slot 166 extending proximally from the distal end 152 toward the handle 158, and having opposing longitudinal edges 168 for slidably retaining the first 106 and the second fixation member 108. As shown, the deployment rod 160 initially rides underneath the second fixation member 108 outside of the lumen at the distal end of the delivery member 156 through which the rod 160 slides. After deployment of the first fixation member 106, a second trigger 163 is engaged which causes a second deployment rod 161 to move distally and push the second fixation member 108 along the slot into a firing position (the position initially occupied by the first fixation member 106) within the lumen and ready to be deployed by the rod 160 when the trigger 162 is engaged. As shown, the delivery member 156 terminates distally in a tissue-penetrating tip 170. Alternatively, the delivery member 156 terminates distally in a blunt tip. In an embodiment, each of the first 106 and the second fixation member 108 is retained on the delivery member 156 in an orientation that presents a minimum cross section of the respective fixation member for insertion into or through tissue along with the delivery member 156.

A resilient tube 172 is shown in FIG. 2A positioned about the delivery member 156. Preferably, the resilient tube 172 is fabricated from a resilient, transparent silicone material. The tube 172 is omitted from FIGS. 2B and C for clarity. The resilient tube is seen to be positioned about the delivery member 156 along a portion of the delivery member encompassing the locations along the delivery member 156 of the first 106 and the second 108 fixation member and at least a portion of the suture therebetween. Friction between the resilient tube 172 and the fixation members 106, 108 and suture retained therein, retains the first 106 and the second fixation members 108 at predetermined longitudinal positions along the delivery member 156 before delivery of the respective fixation members to tissue. The resilient tube 172 similarly provides suture management for the tissue repair assembly 100 by maintaining the suture along the delivery member. A distal end 174 of the resilient tube 172 provides a soft depth stop for insertion of the delivery member 156 into tissue before deploying either or both of the first 106 and the second fixation member 108

FIGS. 3A-3F illustrate an exemplary embodiment of a method for repairing a tissue defect according to the present invention. First referring to FIG. 3A, the delivery member 156, the tissue repair assembly 100 retained thereon, is seen to have been passed through a damaged body tissue 180 having a first tissue surface 182 and a second tissue surface 184, to a first location 186 at the second tissue surface 184, where the first fixation member 106 is seen to have been slidably expelled from the distal end of the delivery member 156, positioning the first fixation member 106 proximate to the first location 186. The damaged body tissue 180 is seen to comprise a tissue defect 188. In an embodiment, the first location 186 is selected by the surgeon so that the completed repair will apply compression to the defect 188. In an embodiment, the tissue defect 188 is a meniscal tear and the compression is effective to close the tear. It is to be noted that for illustrative purposes in FIG. 3A through FIG. 3F, as also noted for FIG. 1 hereinabove, various suture limbs extending from individual fixation members are shown laterally separated from one another through the tissue 180 between the first 182 and the second tissue surface 184, but that in an actual tissue repair, the various suture limbs, follow a substantially common path adjacent to one another through the tissue 102.

Figures 3A, 3B:
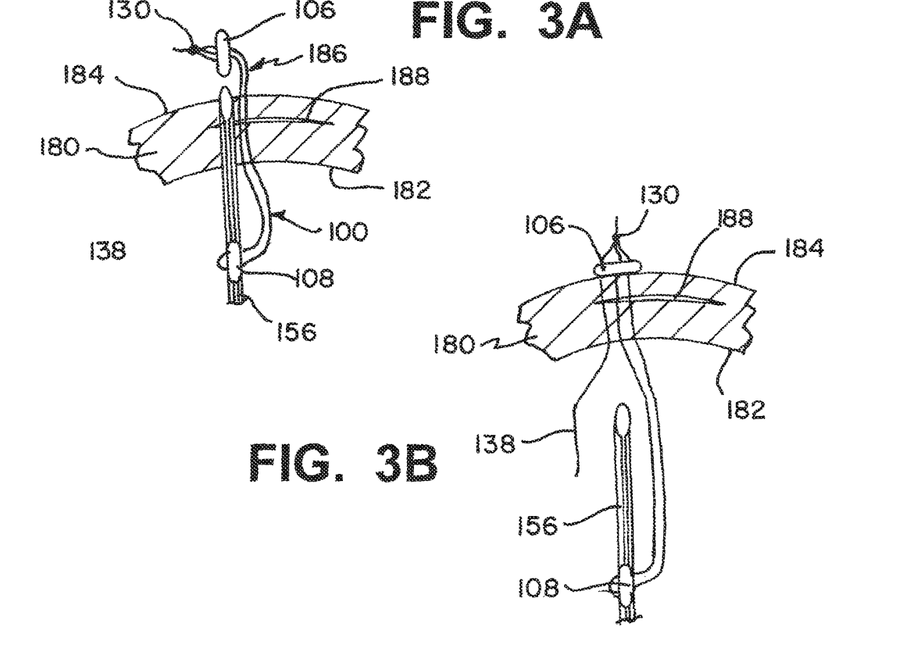
FIGS. 3A-3F are cross-sectional views of an exemplary embodiment of a method for repairing a tissue defect according to the present invention.

Alternatively, the first fixation member 106 can be expelled from the delivery member 156 within the material of the damaged body tissue 180, or within or adjacent to a surface of another body tissue. Depending on the nature and location of the tissue defect 188, the surgeon may elect to pass the deployment member 156 to the first location 186 directly through the tissue defect 188, adjacent to the tissue defect 188, or through another area of tissue where the deployed tissue repair assembly 100 will be effective to apply compression across the tissue defect 188.

Now referring to FIG. 3B, the delivery member 156 is seen to have been retracted from the damaged body tissue 180, leaving the first fixation member 106 proximate to the first location 186. The first fixation member 106, while slidably retained on the delivery member 156, presents a minimum cross section for penetrating tissue. In use, the first fixation member 106 will toggle so that the respective tissue contact surface 112 lodges against the second tissue surface 184 at the first location 186, presenting a maximum cross section of the first fixation device 106 to resist pullout through the damaged tissue 180.

Figures 3C, 3D:
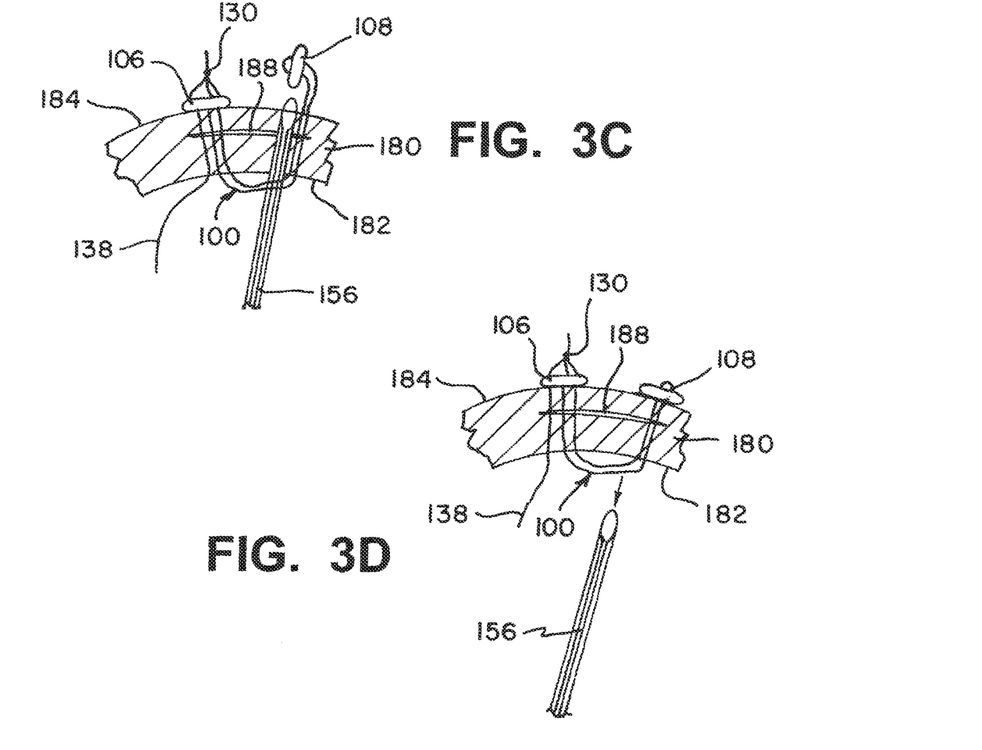

Now referring to FIG. 3C, the delivery member 156, the second fixation member 108 still retained thereon, is seen to have been passed a second time through the damaged body tissue 180, to a second location 190 at the second tissue surface 184, where the second fixation member 108 is seen to have been slidingly expelled from the distal end of the delivery member 156, positioning the second fixation member proximate to the second location 190. The criteria by which the surgeon selects the second location 190 and the path of the delivery member 156 through tissue are parallel to the criteria used to select the first location 186 and the associated path through tissue. Preferably, each of the first 186 and the second location 190 is selected by the surgeon so that the completed repair will apply compression to the tissue defect 188. The second fixation member 108 can be expelled from the delivery member 156 within the material of the damaged body tissue 188, or within or adjacent to a surface of another body tissue.

Turning to FIG. 3D, the delivery member 156 is seen to have been retracted from the damaged body tissue 188, leaving the second fixation member 108 proximate to the second location, and leaving a portion of the suture loop 132 comprising the first suture limb 134 and the second limb 136 positioned adjacent a spanned section 192 of the first tissue surface 182. The second fixation member 108, while slidably retained on the delivery member 156, presents a minimum cross section for penetrating tissue. Upon expulsion from the delivery member 156, and in response to tension applied to one or both of the first limb 134 the second limb 136, the second fixation member 108 toggles so that the respective tissue contact surface 122 lodges against the second tissue surface 184 at the second location 190, presenting a maximum cross section of the second fixation device 108 to resist pullout through the damaged tissue 180.

Figure 3E:
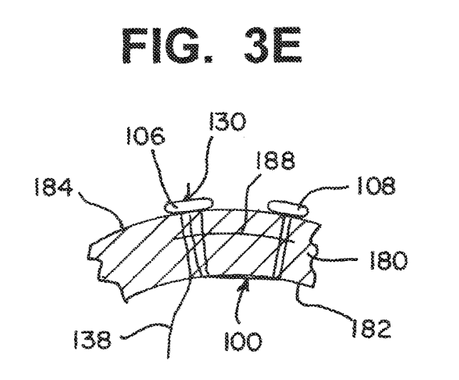

Now turning to FIG. 3E, the tensioning limb 138 is seen to have been tensioned with respect to the first fixation member 106, shortening the suture loop 132 and applying a compressive force to the tissue defect 188. As shown, the tissue defect 188 is a meniscal tear and the compressive force is effective to close the tear. The portion of the suture loop 132 adjacent the spanned section 192 of the first tissue surface 182 remains substantially on the first tissue surface 182 after the tensioning. Preferably, the tensioning causes the suture comprising the loop 132 to locally compress the first tissue surface 182, so that no suture is exposed above the remainder of the first tissue surface 182 with sufficient tensioning the suture comprising the loop 132 embeds into the damaged tissue 180 below the first tissue surface 182, so that no suture is exposed above the remainder of the first tissue surface 182.

Figure 3F:
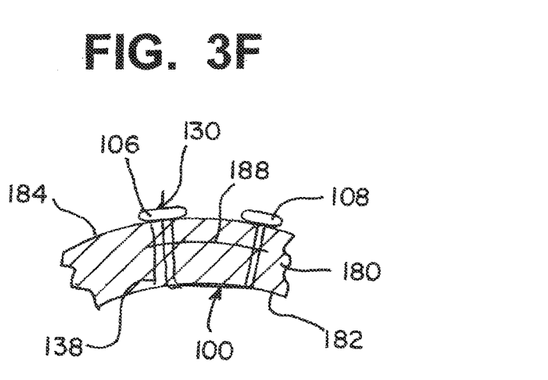

Now turning to FIG. 3F, the tensioning limb 138 is seen to have been trimmed at or below the first tissue surface 182, leaving none of the tensioning limb 138 proud of the first tissue surface 182. As shown, the damaged tissue 180 is a meniscus of a knee, the tissue defect is a meniscal tear, the first tissue surface 182 is the articulating surface of the meniscus, the second tissue surface 184 is the peripheral rim of the meniscus, and each of the first 106 and the second fixation member 108 is deployed in the peripheral meniscal capsule. In other embodiment, two or more tissue repair assemblies of the present invention are used to repair a tissue defect, or to repair physically adjacent defects in a tissue.

The determination by a surgeon of first and second locations for the respective first 106 and second fixation member 108, is dependent on many factors including, but not limited to the type of tissue comprising the defect, the nature and extent of the defect, its location in the tissue, and its proximity to other tissues and other defects that may be present near the surgical site. The first and second locations for respective first and second fixation members can be on a single continuous surface of a damaged tissue. Alternatively, the first and the second location are on opposite sides of a tissue defect along a tissue surface. The first and the second location can be on opposing tissue surfaces, the tissue defect therebetween. The first location and the second location could be on different tissues.

Figure 4A:
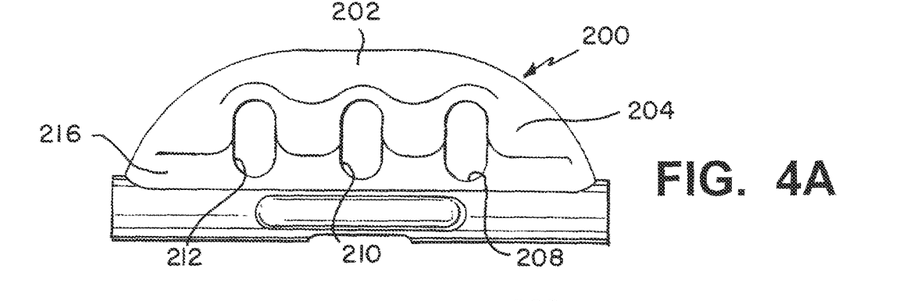
FIGS. 4A-4C are respective top plan, end elevation and side elevation views of an exemplary embodiment of an fixation member of the present invention having three through openings for receiving suture.
Figures 4B, 5B:
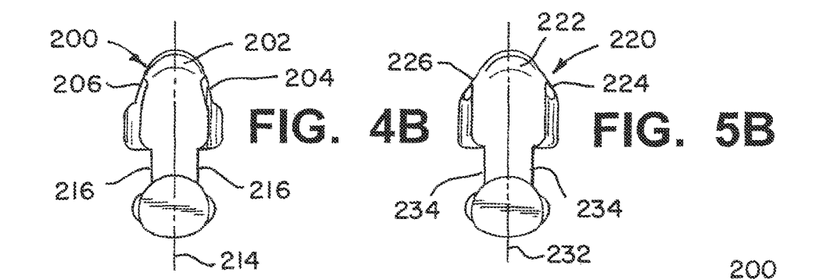
FIGS. 5A-5C are top plan, end elevation and side elevation views of another embodiment of an fixation member of the present invention having two through openings for receiving suture.
Figure 4C:
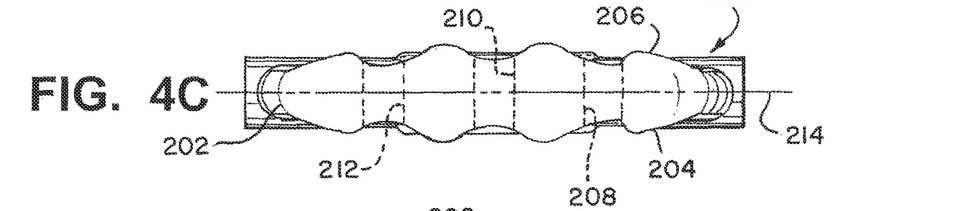

FIGS. 4A-4C schematically illustrate respective top, end and side views of an exemplary embodiment of a three-opening fixation member 200 of the present invention. In an embodiment, the three-opening fixation member 200 is the first fixation member 106 of the tissue repair assembly 100 disclosed hereinabove. The three-opening fixation member 200 is seen to comprise a first body 202 having a respective first surface 204, a respective second surface 206, and three through openings comprising a first 208, a second 210, and a third opening 212 through the body 202 between the respective first surface 204 and second surface 206. In an embodiment, the three-opening fixation member 200 is the first fixation member 106, the respective first surface 204 is the tissue contact surface 112 and the respective second surface 206 is the back surface 114. The three-opening fixation member 200 is symmetrical about a plane 214 between the respective first 204 and second surface 206. Alternatively, the respective first 204 and second surface 206 can be asymmetrical about the plane 214.

Each of the three through openings 208, 210, 212, and one or both of the respective first 204 and second surface 206 adjacent to and therebetween is smoothly rounded to optimize slidability of suture through and between the openings. One or more of the three through openings 208, 210, 212 is elongated in a direction perpendicular to a line interconnecting the one or more opening with an adjacent one of the three through openings. Elongation of the one or more opening enhances the slidability of suture through the respective opening. The first body 202 is also seen to comprise a longitudinal groove 216 on each of the respective first 204 and second surface 206. Each groove 216 is adapted to slidingly engage with one of the edges 168 of the longitudinal slot 166 in the delivery member 156, to retain the three-opening fixation member 200 in the delivery member 156.

Figure 5A:
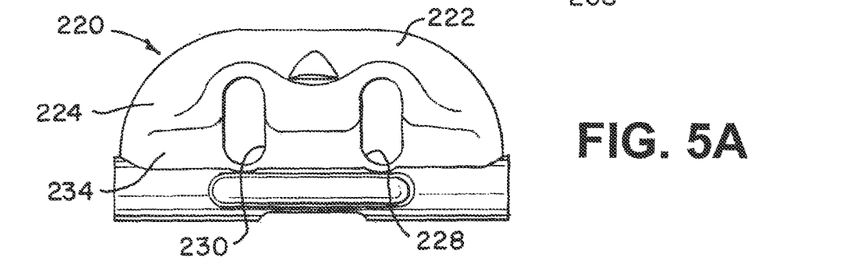
Figure 5C:
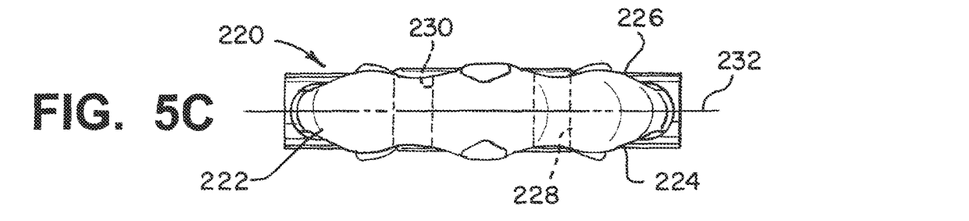

FIGS. 5A-5C schematically illustrate respective top, end and side views of a further embodiment of a two-opening fixation member 220 of the present invention. In an embodiment, the two-opening fixation member 220 is the second fixation member 108 of the tissue repair assembly 100 disclosed hereinabove. Analogous to the three-opening fixation 200 member in construction, the two-opening fixation member 220 is seen to comprise a second body 222 having a respective first surface 224, a respective second surface 226, and two through openings comprising a respective first 228 and second opening 230 through the second body 222 between the respective first surface 224 and second surface 226. The two-opening fixation member 220 is the second fixation member 108, the respective first surface 224 is the tissue contact surface 122 and the respective second surface 226 is the respective back surface 124. The two-opening fixation member 220 is symmetrical about a respective plane 232 between the respective first 224 and second surface 226. Alternatively, the respective first 224 and second surface 226 are asymmetrical about the respective plane 232.

The first 228 and the second through opening 230 in the two-opening fixation member and one or both of the respective first 224 and second surface 226 adjacent to and therebetween are smoothly rounded to optimize slidability of suture through and between the openings. One or both of the two through openings 228, 230 can be elongated in a direction perpendicular to a line interconnecting the two through openings 228, 230 to enhance slidability of suture through the respective openings. The second body 222 is also seen to comprise a respective longitudinal groove 234 on each of the respective first 224 and second surface 226. Each respective groove 234 is adapted to slidingly engage with one of the edges 168 of the longitudinal slot 166 in the delivery member 156, to retain the two-opening fixation member 220 in the delivery member 156.

The three-opening fixation member 200 and the two-opening fixation member 220 can be fabricated from any biocompatible material, and can be of the same, or of a different composition from one another. In one embodiment, at least one of the fixation members 200, 220 is nonabsorbable. In one further embodiment, at least one of the fixation members 200, 220 is fabricated from polyetheretherketone (PEEK) polymer. In another embodiment, at least one of the fixation members 200, 220 is bioabsorbable.

Figure 6:
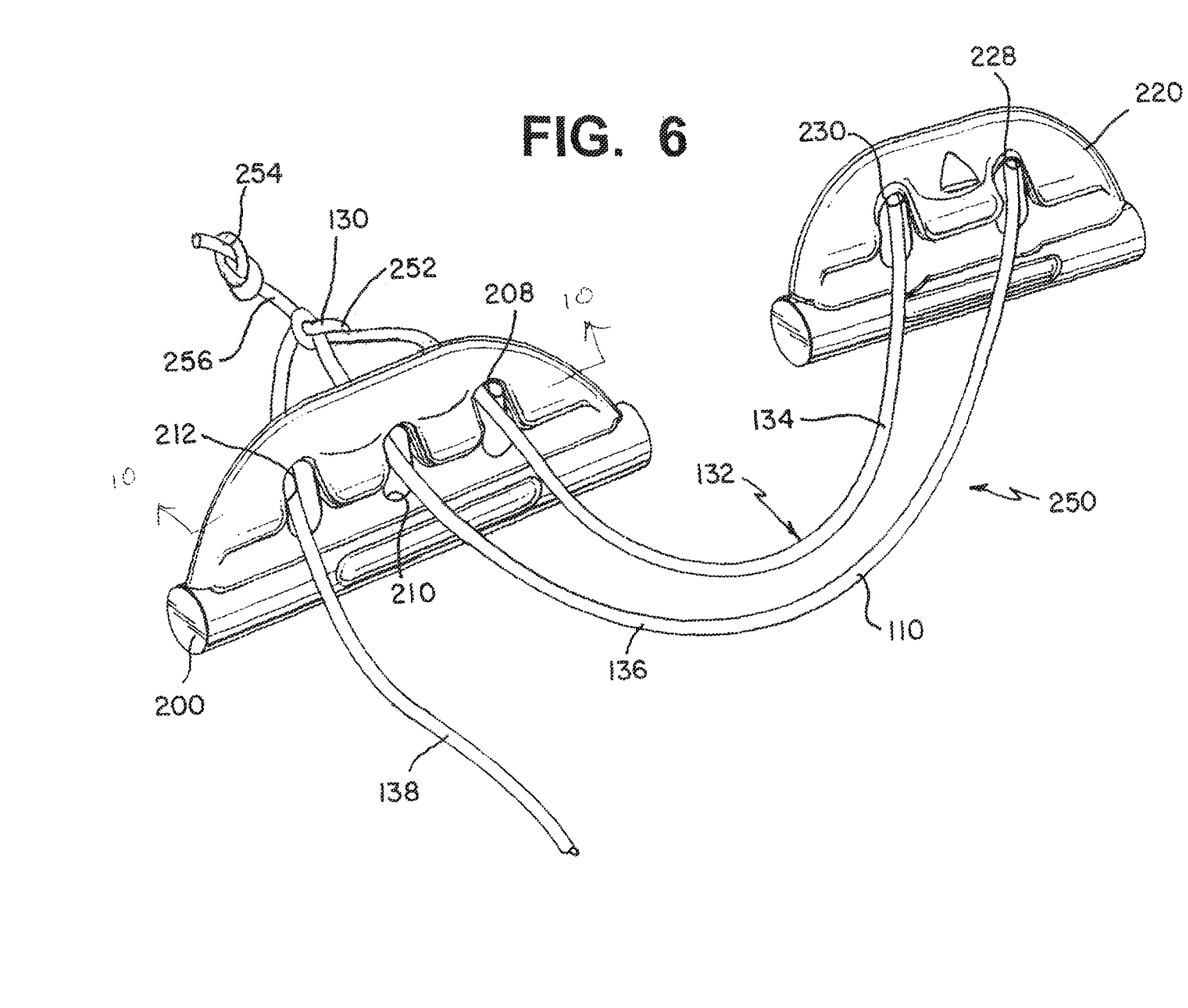
FIG. 6 is a perspective view of a tissue repair assembly of the present invention employing the fixation members of FIGS. 4A-4C and FIGS. 5A-5C.

FIG. 6 schematically illustrates a perspective view of an exemplary embodiment of a tissue repair assembly 250 of the present invention comprising the three-opening fixation member 200 and the two-opening fixation member 220. It has the same construction as the tissue repair assembly 100 disclosed hereinabove, wherein the suture 110 comprises the locking, sliding knot 130, the first 134 the second 136 and the tensioning limb 138, the first 134 and the second limb 136 comprising the suture loop 132.

An engagement portion of the suture 110 is positioned slidingly through the locking, sliding knot 130 at a location, hereinafter, a "post" 252 along the suture 110, substantially adjacent to the respective second surface 206 of the first fixation member 200, between the first 208 and the third opening 212, the post 252 comprising a slidable transition between the first limb 134 and the tensioning limb 136 along the suture 110. Upon tensioning the tensioning limb 138 with respect to the three-opening fixation member 200 to shorten the loop 132, the locking, sliding knot 130 locks the post 252 therein, substantially preventing the loop 132 from lengthening again. Locking, sliding knots are well known in the surgical art. The locking, sliding knot is a bunt line sliding knot, a type of locking, sliding knot known in the surgical arts, as well as in other arts such as nautical arts. Preferably it further comprises a stopper knot 254 to stabilize a suture tail 256 extending from the locking, sliding knot 130. Alternatively, the stopper knot 254 can comprise a single figure eight knot.

The three-opening fixation member 200 and the two-opening fixation member 220 are preferably each fabricated from PEEK, and the suture 110 is a partially bioabsorbable, high strength suture comprising ultra high molecular weight polyethylene (UHMWPE) and polydioxanone (PDS). More preferably, the UHMWPE and PDS suture is an Orthocord™ suture, distributed by Depuy Mitek, of Raynham, Mass.

Figure 7:
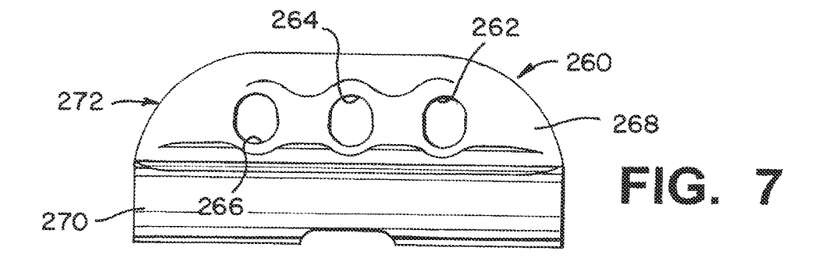
FIG. 7 is a side elevation view of an alternative embodiment of an fixation member of the present invention having three through openings for receiving suture.
Figure 8:
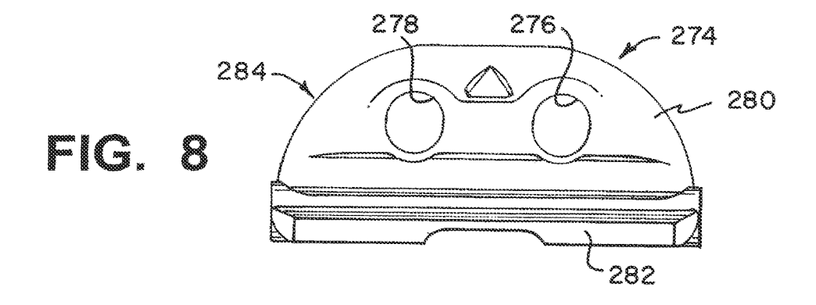
FIG. 8 is a side elevation view of an alternative embodiment of an fixation member of the present invention having two through openings for receiving suture.
Figure 9:
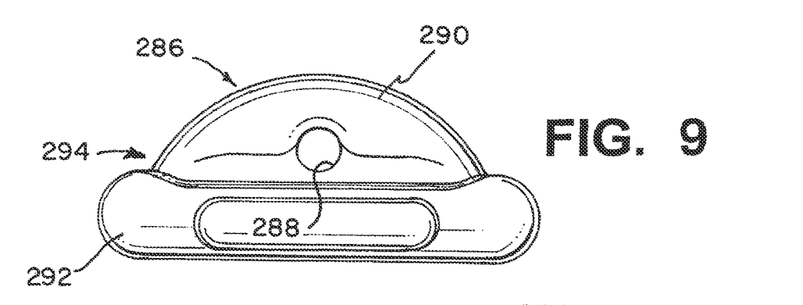
FIG. 9 is a side elevation view of a further embodiment of an fixation member of the present invention having one through opening for receiving suture.

FIG. 7 through FIG. 9 schematically illustrate top views of various alternative embodiments of fixation members that can comprise tissue repair assemblies of the present invention. FIG. 7 illustrates a top view another embodiment of a three-opening fixation member 260 that resembles the fixation member 200 of FIGS. 4A-4C and FIG. 6, except that in the three-opening fixation member 260 illustrated in FIG. 7, each of three openings 262, 264, 266 through a respective body 268 between a respective first 270 and second surface 272, are circular in cross section. Similarly, FIG. 8 illustrates a top view another embodiment of a two-opening fixation member 274 that resembles the fixation member 220 of FIGS. 5A-5C and FIG. 6, except that in the two-opening fixation member 274 illustrated in FIG. 8, each of two openings 276, 278 through a respective body 280 between a respective first 282 and second surface 284 are circular in cross section.

FIG. 9 schematically illustrates an embodiment of a single-opening fixation member 286 of the present invention. The single-opening fixation member 286 is seen to resemble the two-opening fixation member 274 and the three-opening fixation member 260, but having only a single opening 288 through a respective body 290 between a respective first 292 and second surface 294. With reference to the tissue repair assembly 250 comprising the three-opening fixation member 200 and the two-opening fixation member 220, in another embodiment, the two-opening fixation member 220 is replaced with the single-opening fixation member 286, and a suture loop extending between the three-opening fixation member 200 and the single opening fixation member 286, is positioned through the single opening 288.

In further embodiment, a fixation member comprising a tissue repair assembly of the present invention comprises one or more through openings in addition to through openings used to position suture in the construction of the tissue repair assembly. In yet another embodiment, a suture loop extending from a substantially three-opening fixation member comprises two or more fixation members therealong, through each of which the suture loop is positioned.

In tissue fixation assemblies of the present invention, suture is passed substantially in one longitudinal direction only through a locking, sliding element (a restriction element) associated with a fixation member from which three limbs of suture extend. The restriction element can be any type of restriction element through which suture can pass in a preferred longitudinal direction, and is restricted from passing in an opposite longitudinal direction. In various embodiments, the restriction element is a locking, sliding suture knot. In another embodiment, the restriction element comprises one or more opening in the fixation member adapted to pass a barbed suture having a preferred direction of sliding through the one or more opening. In yet another embodiment, the restriction element is a unidirectional passage through or around the fixation member itself.

Figure 10:
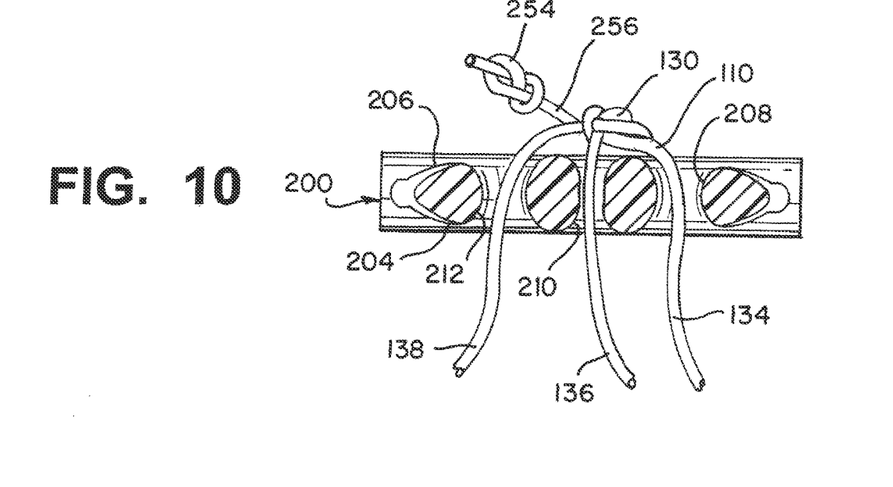
FIG. 10 is a cut-away view taken along lines 10-10 of FIG. 6.

FIG. 10 schematically illustrates a cross sectional side view of a portion of the tissue repair assembly 250 of FIG. 6, showing a cross-sectional view of the three-opening fixation member 200, and the portion of a the suture 110 positioned therethrough, with the locking, sliding knot 130 lodged against the second surface 206. The internal surfaces of the three openings 208, 210, 212 through the three-opening fixation member 200 and the portions of the respective first 204 and second surface 206 therebetween are seen to be rounded to optimize sliding of the suture 110 therethrough and therealong, respectively.

Tissue repair assemblies of the present invention can be constructed in a variety of configurations, comprising fixation members of any size and proportions suited to repairing a particular tissue defect, selection of the size and type of suture used, and variations in the routing of suture with respect to the fixation members. The number of through openings required in fixation members used to construct a tissue repair assembly of the present invention is in turn selected based on the routing of the suture. FIGS. 11A-11F schematically illustrate various alternative embodiments of tissue repair assemblies of the present invention, differing in configuration from the embodiments illustrated hereinabove with regard to one or both of suture routing between two fixation members, and the number of openings provided through the respective fixation members. It is to be noted that the total number of openings provided through any of the fixation members disclosed herein can exceed the number of openings required for a particular suture routing without deviating from the intent or scope of the present invention.

Figure 11:
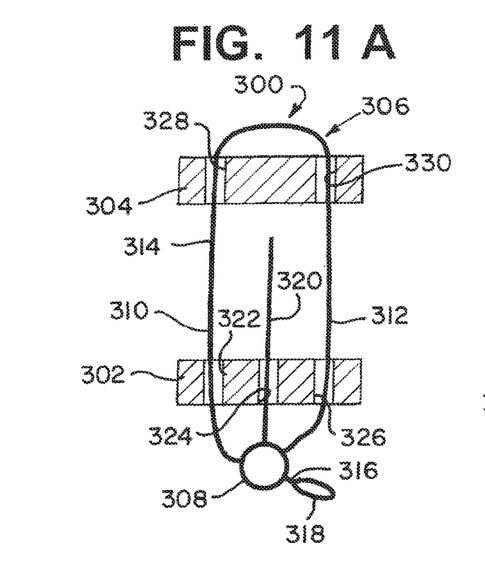
FIGS. 11A-11F are top cut-away views of further embodiments of tissue repair assemblies of the present invention.

FIG. 11A illustrates a first alternative embodiment tissue repair assembly 300 comprising a first fixation member 302 and a second fixation member 304. The tissue repair assembly 300 of FIG. 11A is also seen to comprise a length of suture 306 and a restriction element 308. The restriction element 308 is a locking, sliding knot formed from the suture 306. The length of suture 306 further comprises a first limb 310 continuous with a second limb 312, the first 310 and the second limb 312 together comprising a suture loop 314 connecting the first 302 to the second fixation member 304. The second limb 312 is substantially fixedly connected to the restriction member 308. The second limb 312 extends through the restriction member 308 and is continuous with a suture tail 316 that is terminated by a stopper knot 318 as disclosed hereinabove. The first limb 310 is routed slidingly through the restriction member 308 and is continuous with a tensioning limb 320. In the various embodiments disclosed herein, suture is routed through one or more opening through various fixation members. The suture is generally slidingly routed through the one or more opening to ensure smooth operation of the assembly, for deploying the respective fixation members in tissue, and for sliding suture through the assembly to approximate a tissue defect.

The various alternative embodiments illustrated in each of FIG. 11A through FIG. 11F comprise the length of suture 306 and components thereof, but vary in their routing about and between respective first and second fixation members. As illustrated in FIG. 11A for the first alternative embodiment tissue repair assembly 300, the first fixation member 302 is seen to comprise a first 322, a second 324 and a third opening 326 therethrough. The second fixation member 304 is seen to comprise two openings 328, 330 therethrough. The suture loop 314 is seen to be routed through each of the two openings 328, 330 in the second fixation member 304. The first limb 310 is seen to be routed through the first opening 322 in the first fixation member 302 and to the restriction element 308. The second limb 312 is seen to be routed through the third opening 326 in the first fixation member 302, and to the restriction element 308. The tensioning limb 320 is seen to be routed from the restriction element 308 and through the second opening 324 in the first fixation member 302. Tension applied to the tensioning limb 320 with respect to the first fixation member 302 is effective to draw suture through the restriction member 308, thereby decreasing the size of the loop 314. The tissue repair assembly 300 is seen to resemble the tissue repair assemblies 100, 250 disclosed hereinabove, except that in the embodiment of FIG. 11A, the tensioning limb 320 is routed through a central opening in the respective fixation member 302, as opposed to being routed through a differently positioned in the earlier disclosed tissue repair assemblies 100, 250.

FIG. 11B illustrates a second alternative embodiment of a tissue repair assembly 332 comprising the first 302 and the second fixation member 304 of the embodiment of FIG. 11A, but differing in the suture routing about and through the first fixation member 302, and in construction of the restriction element 308. In an embodiment of the tissue repair assembly 332 of FIG. 11B, the restriction element 308 is a locking, sliding suture knot affixed to the first fixation element 302 by the suture tail 316 being routed through the third opening 326 in the first fixation device 302 and secured therethrough by the stopper knot 318. Each of the first 310 and the second limbs of suture 312 are seen to be routed through one of the first 322 and the second openings 324 in the first fixation member 302. Further, in the embodiment of FIG. 11B, the tensioning limb 320 is seen to be routed around the first fixation member 302, as opposed to being routed through an opening in the first fixation member 302, as illustrated for the first alternative embodiment of the tissue repair assembly 300 illustrated in FIG. 11A.

FIG. 11C illustrates a third alternative embodiment of a tissue repair assembly 334. The tissue repair assembly 334 of FIG. 11C is seen to comprise a first fixation member 336 having a first 338 and a second opening 340 therethrough. The tissue repair assembly 334 is also seen to comprise a second fixation member 342 having a single opening 344 therethrough. The suture loop 314 is seen to be routed through the single opening 344 in the second fixation member 342, and each of the first 310 and the second limb 312 of suture is seen to be routed through one of the first 338 and the second opening 340 in the first fixation member 336. As in the suture routing illustrated for the embodiment of FIG. 11B, the tensioning limb 320 is seen to be routed around the first fixation member 336.

A fourth alternative embodiment of a tissue repair assembly 346 is illustrated in FIG. 11D. The tissue repair assembly 346 illustrated in FIG. 11D resembles the tissue repair assembly 334 illustrated in FIG. 11C, except that in the embodiment illustrated in FIG. 11D, the tensioning limb 320 is routed from the restriction element 314, through the second opening 340 in the first fixation member 336. In addition, one of the first 310 and the second limb of suture 312 is seen to be routed through the first opening 338 in the first fixation member 336, and the other of the first 310 and the second limb of suture 312 is seen to be routed around the first fixation member 336.

Figure 11E:
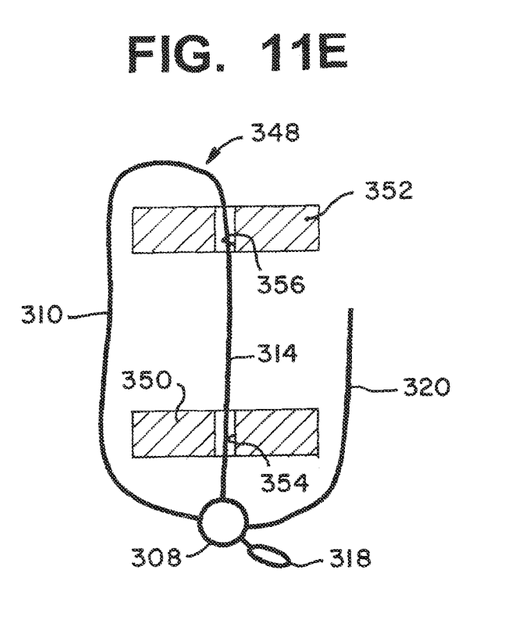

FIG. 11E illustrates a fifth alternative embodiment of a tissue repair assembly 348 comprising a first 350 and a second fixation member 352 each having a single respective opening 354, 356 therethrough. In this embodiment, the suture loop 320 is seen to be routed through the single opening 356 in the second fixation member 352. One of the first 310 and the second limb of suture 312 is seen to be routed through the single opening 354 in the first fixation member 350, and the other of the first 310 and the second limb of suture 312 is seen to be routed around the first fixation member 350. In addition, the tensioning limb 320 is seen to be routed around the first fixation member 350.

Figure 11F:
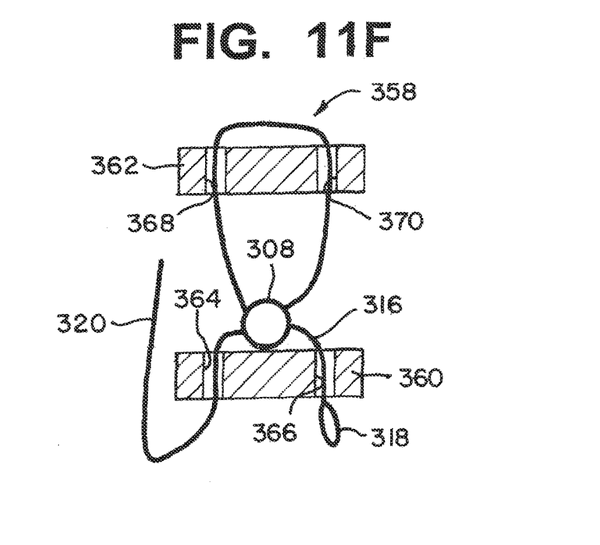

FIG. 11F illustrates a sixth alternative embodiment of a tissue repair assembly 358 comprising a first 360 and a second fixation member 362, each having two respective openings 364, 366, 368, 370 therethrough. The suture loop 314 is seen to be routed through each of the two openings 368, 370 in the second fixation member 362 and each of the first 310 and the second suture limb 312 is routed directly to the restriction member 308, which is positioned adjacent to the first fixation member 360, between the first 360 and the second fixation member 362. The restriction element 308 is a locking, sliding suture knot affixed to the first fixation member 360 by the suture tail 316 being routed through one 366 of the two respective openings 364, 366 in the first fixation device 360 and secured therethrough by the stopper knot 318. The tensioning limb 320 is seen to be routed through the other 364 of the two respected openings 364, 366 in the first fixation device 360.

It is to be noted that in any of the embodiments disclosed herein, any of the embodiments of respective second fixation members can be combined with any of the embodiments of respective first fixation members, associated restriction elements and suture routing to provide additional embodiments within the intent and scope if the present invention.

Tissue repair assemblies and methods of the present invention have several advantages. A meniscal repair procedure using a tissue repair assembly of the present invention can provide a finished tissue repair where only suture, no hard bodies or knots, are left on the articulating (that surface facing the femur) surface of the meniscus in the knee, thus supporting healing and minimizing the probability that articulating cartilage contacting the meniscus will be damaged when the patient flexes the knee joint after the surgery. Also advantageously, the repairs can be performed in any orientation with respect to a damaged tissue and the associated tissue defect. Tissue repair assemblies of the present invention provide additional flexibility for the surgeon because the tissue repair assemblies include no fixed lengths of suture to limit the relative locations of the two tissue fixation members. For example, a repair performed using the tissue repair assemblies of the present invention do not restrict the minimum distance between the two fixation members. Importantly, using tissue repair assemblies of the present invention, an entire meniscal repair can be performed from the articulating side of the meniscus, an approach that minimizes surgical trauma to surrounding tissue.

Another advantage is that the strength and stability of a repair performed using tissue repair assemblies of the present invention is provided by two uninterrupted, continuous limbs of suture, the limbs including no joints, knots, or retainers therealong between first and second anchoring members. Further advantageously, providing two sutures that completely span the anchoring locations provides superior distribution of forces on the repaired tissue, relative to single, knotted or joined suture segments spanning the anchoring locations.

Tissue repair assemblies of the present invention are also very versatile in their application, including applicability to meniscal repairs, approximation of partial shoulder rotator cuff tears, and any other soft tissue repair where two tissues, or damage within a tissue, requires surgical approximation. In addition, by pre-drilling one or more hole in bone for insertion of the delivery member, the tissue repair assemblies could be used to anchor soft tissue to bone While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An apparatus comprising:

first and second fixation members, the first fixation member having a first surface, an opposing second surface, first, second and third through openings defined between the first surface and the second surface;

a flexible element coupling the first and the second fixation members, the flexible element having a first end, a second end and a length therebetween, the length extending from the first end, in order, along a first end section of suture, through the first opening in the first fixation member from the respective first surface to the respective second surface, to and slideably connecting to the second fixation member, through the second opening in the first fixation member from the respective second surface to the respective first surface, and along a second end section of suture;

a sliding, locking knot formed between the first end section and the second end section, the first end section positioned slidably through the knot, the first end section extending from the knot and through the third opening from the first surface to the second surface and wherein tension applied to the first end section with respect to the first fixation member is effective to decrease a length of the flexible element between the first and the second fixation member along the flexible member coupling the first and the second fixation member.

2. The apparatus according to claim 1 wherein the first, second and third openings through the first fixation member are arranged in substantially a straight line along the respective first and second surface.

3. The apparatus according to claim 1 wherein the first fixation member comprises rounded surfaces between the first, second and third through openings, for sliding the flexible element therealong.

4. The apparatus according to claim 1 further comprising a delivery device having an elongated delivery member within which at least a portion of each of the first and the second fixation members, coupled by the flexible element, is longitudinally and slidably received.

5. The apparatus according to claim 1 wherein the flexible element comprises a suture.

6. The apparatus according to claim 1 wherein the flexible element comprises polyethylene.

7. The apparatus according to claim 1 wherein the flexible element comprises polyethylene and a bioabsorbable polymer.

8. The apparatus according to claim 7 wherein the bioabsorbable polymer comprises polydioxanone.

9. The apparatus according to claim 1 wherein the sliding, locking knot is a bunt line knot.

* * * * *